United States Patent [19]

Nyfeler

[11] Patent Number: 4,567,052
[45] Date of Patent: Jan. 28, 1986

[54] 3-PHENYL-4-CYANOPYRROLE DERIVATIVES, THE PREPARATION THEREOF, AND METHOD OF USE THEREOF AS MICROBICIDES

[75] Inventor: Robert Nyfeler, Basel, Switzerland

[73] Assignee: Ciba-Geigy Corporation, Ardsley, N.Y.

[21] Appl. No.: 618,867

[22] Filed: Jun. 8, 1984

[30] Foreign Application Priority Data

Jun. 17, 1983 [SE] Sweden ................................. 833331
May 10, 1984 [SE] Sweden ................................. 842304

[51] Int. Cl.$^4$ ...................... A23L 3/34; C07D 207/30; C07D 307/02; C07D 407/00
[52] U.S. Cl. ................................... 426/532; 548/561; 549/414; 549/473
[58] Field of Search ................ 548/561; 549/414, 473; 426/532

[56] References Cited

U.S. PATENT DOCUMENTS

| | | | |
|---|---|---|---|
| 3,709,906 | 1/1973 | Yoshida et al. | 548/561 |
| 3,864,491 | 2/1975 | Bailey | 548/561 |
| 3,932,458 | 1/1976 | Bailey | 548/561 |
| 4,229,465 | 10/1980 | Ohkuma et al. | 548/561 |
| 4,431,823 | 2/1984 | Fryer et al. | 548/561 |

FOREIGN PATENT DOCUMENTS 56-79672 6/1981 Japan .
2078761 1/1982 United Kingdom .

OTHER PUBLICATIONS van Leusen et al., Tetrahedron Letters, No. 52, pp. 5337–5340 (1972).
Anderson et al.–Canadian Jour. Chem., vol. 56, No. 5 (Mar. 1978), pp. 654–657.

Primary Examiner—Herbert S. Cockeram
Attorney, Agent, or Firm—Edward McC. Roberts; Irving M. Fishman

[57] ABSTRACT

The invention relates to novel N-alkylated 3-phenyl-4-cyanopyrrole derivatives of the formula I

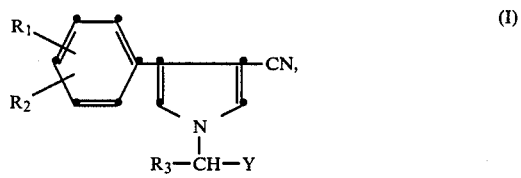

wherein
$R_1$ and $R_2$, each independently of the other, are hydrogen, halogen, methoxy or methylthio,
$R_3$ is hydrogen or $C_1$-$C_8$haloalkyl,
Y is hydroxy, halogen or the —O—C(O)—$R_4$ group, and
$R_4$ is hydrogen, $C_1$-$C_8$alkyl, $C_1$-$C_8$haloalkyl, $C_2$-$C_6$alkenyl, 2-tetrahydrofuryl, 2-tetrahydropyranyl, $C_1$-$C_6$alkoxycarbonyl or the —CH($R_5$)—$XR_6$ group, wherein
X is oxygen or sulfur,
$R_5$ is hydrogen or $C_1$-$C_3$alkyl, and
$R_6$ is $C_1$-$C_6$alkyl, ($C_1$-$C_6$alkoxy)-$C_1$-$C_6$alkyl, $C_3$-$C_6$alkenyl, $C_3$-$C_6$alkynyl, phenyl or phenyl which is substituted by halogen, $C_1$-$C_6$alkyl, $C_1$-$C_6$alkoxy, or $C_1$-$C_6$alkoxycarbonyl.

The invention also relates to the preparation of these compounds by N-alkylation of the starting pyrroles, as well as to microbicidal compositions which contain a compound of formula I as active ingredient. Also disclosed is a method of controlling phytopathogenic micro-organisms which comprises the use of the novel compounds.

10 Claims, No Drawings

3-PHENYL-4-CYANOPYRROLE DERIVATIVES, THE PREPARATION THEREOF, AND METHOD OF USE THEREOF AS MICROBICIDES

The present invention relates to novel N-alkylated 3-phenyl-4-cyanopyrrole derivatives of the formula I below, to the preparation thereof, and to microbicidal compositions which contain at least one of the novel compounds. The invention further relates to the preparation of said compositions and to the use of the novel compounds and compositions for controlling harmful micro-organisms, in particular phytopathogenic fungi.

Specifically, the invention relates to novel compounds of the general formula I

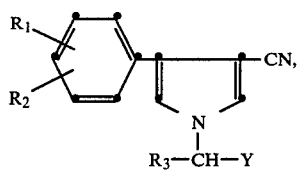

wherein $R_1$ and $R_2$, each independently of the other, are hydrogen, halogen, methoxy or methylthio, $R_3$ is hydrogen or $C_1-C_8$haloalkyl, Y is hydroxy, halogen or the —O—C(O)—$R_4$ group, and $R_4$ is hydrogen, $C_1-C_8$alkyl, $C_1-C_8$haloalkyl, $C_2-C_6$alkenyl, 2-tetrahydrofuryl, 2-tetrahydropyranyl, $C_1-C_6$alkoxycarbonyl or the —CH($R_5$)—$XR_6$ group, wherein X is oxygen or sulfur, $R_5$ is hydrogen or $C_1-C_3$alkyl, and $R_6$ is $C_1-C_6$alkyl, ($C_1-C_6$alkoxy)-$C_1-C_6$alkyl, $C_3-C_6$alkenyl, $C_3-C_6$alkynyl, phenyl or phenyl which is substituted by halogen, $C_1-C_6$alkyl, $C_1-C_6$alkoxy or $C_1-C_6$alkoxycarbonyl.

Depending on the indicated number of carbon atoms, alkyl by itself or as moiety of another substituent comprises e.g. the following groups: methyl, ethyl, propyl, butyl, pentyl, hexyl etc., and the isomers thereof, e.g. isopropyl, isobutyl, tert-butyl, isopentyl etc. Haloalkyl denotes a mono- to prehalogenated alkyl substituent, e.g. $CH_2Cl$, $CHCl_2$, $CCl_3$, $CH_2Br$, $CHBr_2$, $CBr_3$, $CHF_2$, $CF_3$, $CCl_2F$, $CCl_2$—$CHCl_2$, $CH_2CH_2F$, $CI_3$ etc. In formula I and throughout this specification halogen denotes fluorine, chlorine, bromine or iodine, with fluorine, chlorine or bromine being preferred. Alkenyl is e.g. vinyl, 1-propenyl, allyl, 1-butenyl, 2-butenyl, 3-butenyl etc., as well as alkyl chains which are interrupted by several C=C double bonds. Alkinyl is e.g. 2-propynyl, propargyl, 1-butynyl, 2-butynyl etc., with propargyl being preferred.

The compounds of formula I are oils, resins or mainly crystalline solids which are stable under normal conditions and have extremely valuable microbicidal properties. They can be used in particular under field conditions in agriculture or related fields curatively and, most particularly, preventively for controlling phytopathogenic micro-organisms. The compounds of formula I exhibit excellent fungicidal properties when applied in wide ranges of concentration and their use in the field poses no problems.

In increasing order of preference, the following groups of compounds are preferred on account of their pronounced microbicidal activity:

(a) compounds of the formula I, wherein $R_1$ is in the 2-position and $R_2$ is in the 3-position of the phenylring and each independently of the other is hydrogen, halogen, methoxy or methylthio; $R_3$ is hydrogen or $C_1-C_4$haloalkyl; and Y is hydroxy, halogen or the —O—C(O)—$R_4$ group, wherein $R_4$ is $C_1-C_6$alkyl, $C_1-C_6$haloalkyl, 2-tetrahydrofuryl, 2-tetrahydropyranyl, $C_1-C_2$alkoxycarbonyl or the —CH($R_5$)—$XR_6$ group, wherein X is oxygen or sulfur, $R_5$ is hydrogen or methyl and $R_6$ is $C_1-C_6$alkyl, ($C_1-C_3$alkoxy)-$C_1-C_3$alkyl, $C_3-C_6$alkenyl, $C_3-C_6$alkynyl, phenyl or phenyl which is substituted by fluorine, chlorine, bromine, methyl, methoxy and/or $C_1-C_3$alkoxycarbonyl;

(b) compounds of the formula I, wherein $R_1$ is hydrogen, 2-Cl, 2-methoxy or 2-methylthio; $R_2$ is hydrogen or 3-Cl; $R_3$ is hydrogen or $C_1-C_4$haloalkyl; and Y is OH, chlorine or the —O—C(O)—$R_4$ group, wherein $R_4$ is $C_1-C_4$alkyl, $C_1-C_3$haloalkyl, 2-tetrahydrofuryl, 2-tetrahydropyranyl, $C_1-C_2$alkoxycarbonyl or the —CH$_2$—$OR_6$ group, wherein $R_6$ is $C_1-C_4$alkyl, ($C_1-C_3$alkoxy)-$C_1C_3$alkyl, $C_3-C_6$alkenyl, $C_3-C_6$alkynyl, phenyl or phenyl which is substituted by fluorine, chlorine, bromine, methyl, methoxy, ethoxycarbonyl and/or methoxycarbonyl;

(c) compounds of the formula I, wherein $R_1$ is hydrogen, 2-Cl, 2-methoxy or 2-methylthio; $R_2$ is hydrogen or 3-Cl; $R_3$ is hydrogen or $CCl_3$; and Y is OH, chlorine or the —O—C(O)—$R_4$ group, wherein $R_4$ is $C_1-C_4$alkyl, $C_1-C_2$haloalkyl, 2-tetrahydrofuryl, 2-tetrahydropyranyl, methoxycarbonyl or the —$CH_2OR_6$ group, wherein $R_6$ is $C_1-C_4$alkyl, methoxymethyl, ethoxymethyl, methoxyethyl, allyl, propargyl, phenyl or phenyl which is substituted by fluorine, chlorine, bromine, methyl, methoxy and/or methoxycarbonyl.

The following individual compounds (a) to (u) are particularly preferred on account of their marked fungicidal properties under field conditions:

(a) N-(hydroxymethyl)-3-(3-chlorophenyl)-4-cyanopyrrole, (b) N-(1-acetyloxy-2,2,2-trichloroethyl)-3-(2,3-dichlorophenyl)-4-cyanopyrrole, (c) N-(1-hydroxy-2,2,2-trichloroethyl)-3-(2-methylthiophenyl)-4-cyanopyrrole, (d) N-(1-hydroxy-2,2,2-trichloroethyl)-3-(2,3-dichlorophenyl)-4-cyanopyrrole, (e) N-(1-hydroxy-2,2,2-trichloroethyl)-3-(2-methoxyphenyl)-4-cyanopyrrole, (f) N-(1-methoxyacetyloxy-2,2,2-trichloroethyl)-3-(2,3-dichlorophenyl)-4-cyanopyrrole, (g) N-(1-hydroxy-2,2,2-trichloroethyl)-3-(3-methoxyphenyl)-4-cyanopyrrole, (h) N-(methoxyacetyloxymethyl)-3-(2,3-dichlorophenyl)-4-cyanopyrrole, (i) N-(1-hydroxy-2,2,2-trichloroethyl)-3-(2-chlorophenyl)-4-cyanopyrrole, (k) N-(chloromethyl)-3-(3-methoxyphenyl)-4-cyanopyrrole, (l) N-[1-(n-butylcarbonyloxy)-2,2,2-trichloroethyl]-3-(2,3-dichlorophenyl)-4-cyanopyrrole, (m) N-(1,2,2,2-tetrachloroethyl)-3-(3-methoxyphenyl)-4-cyanopyrrole, (n) N-[1-(n-propoxyacetyloxy)-2,2,2-trichloroethyl]-3-(2,3-dichlorophenyl)-4-cyanopyrrole, (o) N-(1,2,2,2-tetrachloroethyl)-3-(3-bromophenyl)-4-cyanopyrrole, (p) N-[1-(n-butoxyacetyloxy)-2,2,2-trichloroethyl]-3-(2,3-dichlorophenyl)-4-cyanopyrrole, (q) N-[1-(isopropoxyacetyloxy)-2,2,2-trichloroethyl]-3-(2-chlorophenyl)-4-cyanopyrrole, (r) N-[1-(n-butoxyacetyloxy)ethyl]-3-(2,3-dichlorophenyl)-4-cyanopyrrole, (s) N-[1-(methoxyacetyloxy)-2,2,2-trichloroethyl]-3-(2-methylthiophenyl)-4-cyanopyrrole, (t) N-[1-(propargyloxyacetyloxy)-2,2,2-trichloroethyl]-3-(2,3-dichlorophenyl)-4-cyanopyrrole, (u) N-(methoxyacetyl)-3-(2-chlorophenyl)-4-cyanopyrrole.

The novel compounds of the formula I are prepared by converting a 3-phenyl-4-cyanopyrrole derivative of the formula II

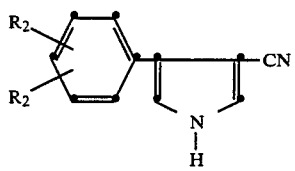
(II)

by reaction with an aldehyde of the formula III

$R_3$—CHO  (III)

into a hydroxy derivative of the formula Ia

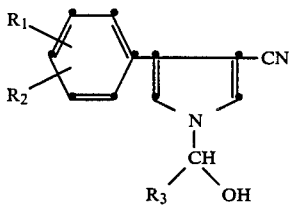
(Ia)

and, if desired, converting said derivative into another compound of the formula I by replacing the free OH group by another radical Y, said replacement being effected by converting either a compound of the formula Ia with an acid of the formula IV $R_4$—COOH  (IV)

or preferably with a reactive acid derivative thereof, in particular an acid halide, e.g. an acid chloride or acid bromide, or with the acid anhydride thereof, into an acyloxy compound of the formula Ib

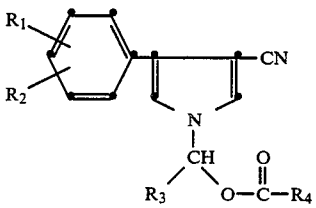
(Ib)

or, in a compound of the formula Ia, replacing the free OH group first by a halogen atom, preferably a chlorine or bromine atom, in conventional manner and, if desired, converting the so halogenated compound by reaction with a salt of the formula V

$R_4$—COO$^\ominus$M$^+$  (V)

into a compound of the formula Ib, in which formulae above the substituents are as defined for formulae Ia, Ib, II, III, IV and V, M⊕ is a metal cation, preferably the cation of an alkaline earth metal or, preferably, of an alkali metal, and is e.g. Ca⊕⊕, Mg⊕⊕, Na⊕ or K⊕.

The reaction of a compound of formula II with an aldehyde of the formula III can be carried out in the presence or absence of an inert solvent or mixture of solvents. Examples of suitable solvents are: aromatic hydrocarbons such as benzene, toluene or xylenes; halogenated hydrocarbons such as chlorobenzene; aliphatic hydrocarbons such as petroleum ether; ether and ethereal compounds such as dialkyl ethers (diethyl ether, diisopropyl ether, tert-butylmethyl ether etc.), furan, dimethoxyethane, dioxan, tetrahydrofuran; and dimethylformamide and the like.

The reaction of the compounds of formula II with compounds of formula III is conveniently carried out without a solvent but using an excess of the aldehyde of formula III. Depending on the nature of the aldehyde of the formula III, the reaction is carried out in solution or in the melt. The reaction rate can be speeded up by adding an acid or basic catalyst. Examples of suitable acid catalysts are non-aqueous hydrogen halides and mineral acids such as HCl, HBr or H$_2$SO$_4$, and also concentrated hydrochloric acid. Examples of suitable basic catalysts which can be used are: trialkylamines such as trimethylamine, triethylamine, dimethylethylamine etc., alkali metal carbonates and alkaline earth metal carbonates such as Na$_2$CO$_3$, BaCO$_3$, MgCO$_3$, K$_2$CO$_3$ etc., or alkali metal alcoholates such as NaOCH$_3$, NaOC$_2$H$_5$, KO(iso-C$_3$H$_7$), KO(tert-butyl). The reaction temperatures are normally in the range from 0° to +200° C., preferably from 0° to +160° C., and the reaction time is from 1 to 24 hours, preferably from 1 to 4 hours.

The reaction to replace the free hydroxyl group in the compounds of formula Ia by a group Y is preferably carried out in an inert solvent. Examples of such solvents are: aromatic and aliphatic hydrocarbons such as benzene, toluene, xylenes, petroleum ether, ligroin or cyclohexane; halogenated hydrocarbons such as chlorobenzene, methylene chloride, ethylene chloride, chloroform, carbon tetrachloride or tetrachloroethylene; ethers and ethereal compounds such as diethyl ether, diisopropyl ether, tert-butylmethyl ether, dimethoxyethane, dioxan, tetrahydrofuran or anisole; esters such as ethyl acetate, propyl acetate or butyl acetate; nitriles such as acetonitrile; or compounds such as dimethylsulfoxide, dimethylformamide, and mixtures of such solvents with one another.

The introduction of the group Y is effected by conventional methods. If Y is chlorine, the reagent employed is e.g. phosphoroxy chloride, phosphorus trichloride, phosphorous pentachloride or, preferably, thionyl chloride. The reaction is normally carried out in the temperature range from 0° to +120° C. If Y is bromine, the preferred reagent is phosphorus tribromide or phosphorus pentabromide and the reaction is carried out in the temperature range from 0° to +50° C. If Y is the —O—C(O)—R$_4$ group, the reagent employed will normally be the corresponding acid halide, preferably acid chloride. In this case it is best to carry out the reaction in the temperature range from −20° to +50° C., preferably from −10° to +30° C., and in the presence of a weak base such as pyridine or triethylamine. To speed up the reaction it is also possible to add a 4-dialkylaminopyridine such as 4-dimethyl- or 4-dimethylaminopyridine as catalyst.

The reaction of compounds of formula I, wherein Y is halogen, preferably chlorine or bromine, with salts of formula V is usually carried out in the presence of a commonly employed inert solvent or mixture of solvents. Examples of such solvents are: aromatic and aliphatic hydrocarbons such as benzene, xylenes, petroleum ether, ligroin or cyclohexane; ethers and ethereal compounds such as dialkyl ethers, e.g. diethyl ether, diisopropyl ether, tert-butylmethyl ether, dimethoxyethane, dioxan, tetrahydrofuran or anisol; esters such as ethyl acetate, propyl acetate or butyl acetate; nitriles such as acetonitrile; or compounds such as dimethylsulfoxide, dimethylformamide and mixtures of such solvents with one another.

The course of this reaction can be advantageously influenced by addition of catalytic amounts of a crown ether, e.g. 18-crown-6 or 15-crown-5. The reaction temperature is generally in the range from 0° to +150° C., preferably from +20° to +80° C. The reaction time is from 1 to 24 hours.

In a preferred embodiment, the preparation of compounds of formula Ib, in particular those in which $R_3$ is $CCl_3$ or $R_3$ is H, starting from compounds of formula II, is effected by carrying out the reaction continuously without isolation of the intermediate formed. This reaction is conveniently carried out in one of the solvents or diluents referred to above, most suitably e.g. an ethereal compound such as tetrahydrofuran, and in the presence of a weak base such as a trialkylamine, e.g. triethylamine, or pyridine. Chloral or paraformaldehyde is used as reagent. The reaction can be speeded up by adding a catalyst such as 1,8-diazabicyclo[5.4.0]undec-7-ene. The temperature in this first reaction step is in the range from −20° to +100° C., preferably from 0° to +50° C., and the reaction time is from ½ hour to 2 hours. A hydroxy derivative of the formula Ia is obtained as intermediate. This intermediate is not isolated, but is reacted with a compound of the formula IV, in the same reaction solution, in the temperature range from −30° to +30° C., preferably from −10° to 0° C., and in the presence of catalytic amounts of a 4-dialkylaminopyridine, preferably 4-dimethylaminopyridine. The reaction time of this second step is from ½ hour to 16 hours.

The starting materials of the formulae III, IV and V are generally known or they can be prepared by methods which are known per se.

Some of the pyrroles of the formula II are known from the literature. Thus, for example, the method of preparing 4-cyano-3-phenylpyrrole and the chemical properties thereof are described in Tetrahedron Letters No. 52. pp. 5337–5340 (1972). No mention is made of the biological properties of this compound.

N-Acetylated, substituted 3-phenyl-4-cyanopyrroles are known from the literature. For example, pyrroles of the formula VI

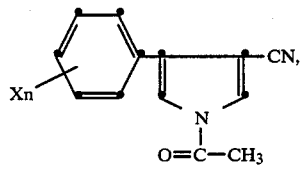

(VI)

wherein X is a halogen atom, a lower alkyl group or lower haloalkyl group, and n is 0, 1 or 2, are described as fungicides in DE-OS 2 927 480.

Pyrrole derivatives of the formula VII

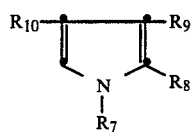

(VII)

wherein
$R_7$=acyl, alkoxycarbonylalkyl . . .
$R_8$, $R_9$=H, aryl . . .
$R_{10}$=hydroxy, mercapto
are known as heat and light stabiliers for PVC plastics from GB Pat. No. 2 078 761.

Further pyrrole derivatives of the formula VIII

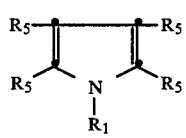

(VIII)

wherein
$R_1$=alkyl, unsubstituted or substituted by acyloxy . . .
$R_5$=H, alkyl, CN . . .
are known as polymerisation catalysts for vinyl chloride from DE-OS No. 2 028 363.

The known pyrrole derivatives are either inactive to phytopathogens or in the greenhouse they have a marked fungicidal activity which is not reproduced under field conditions owing to their instability to environmental influences. They are therefore not suitable for practical application in agriculture, in horticulture or in related fields of use. In contradistinction thereto, the novel pyrrole derivatives of the formula I constitute a useful enlargement of technical knowledge, for it has surprisingly been found that they have, for practical field application purposes, a very advantageous microbicidal activity spectrum against phytopathogenic fungi and bacteria. They can be used not only in crop growing or similar fields of use for controlling harmful micro-organisms in cultivated plants, but additionally in storage protection for preserving perishable goods. Compounds of formula I have very advantageous curative, systemic and, in particular, preventive properties, and can be used for protecting numerous cultivated plants, in particular field crops. With the compounds of formula I it is possible to inhibit or destroy the micro-organisms which occur in plants or in parts of plants (fruit, blossoms, leaves, stems, tubers, roots) in different crops of useful plants, while at the same time the parts of plants which grow later are also protected from attack by such micro-organisms.

The compounds of formula I are effective for example against the phytopathogenic fungi belonging to the following classes: Ascomycetes, e.g. Erysiphe, Sclerotinia, Fusarium, Monilinia, Helminthosporium; Basidiomycetes, e.g. Puccinia, Tilletia, Rhizoctonia; as well as the Oomycetes belonging to the class of Phycomycetes, e.g. Phytophthora. As plant protective agents, the compounds of formula I can be used with particular success against important noxious fungi of the Fungi imperfecti family, e.g. against Cercospora, Piricularia and, in particular, against Botrytis spp. (B. cinerea, B. allii) and the grey mould on vines, strawberries, apples, onions and other varieties of fruit and vegetables is a noxious fungus that causes considerable economic damage. Furthermore, some compounds of the formula I, e.g. compound 1.2, can be successfully used for protecting perishable goods of vegetable or animal origin. They control mould fungi such as Penicillium, Aspergillus, Rhizopus, Fusarium, Helminthosporium, Nigrospora and Alternaria, as well as bacteria such as butyric acid bacteria and yeast fungi such as Candida.

As plant protective agents, the compounds of formula I have a very advantageous activity spectrum for practical application in agriculture for protecting cultivated plants, without damaging said plants by harmful side-effects. They can also be used as seed dressing agents for protecting seeds (fruit, tubers, grains) and plant cuttings against fungus infections and against phytopathogenic fungi which occur in the soil.

Accordingly, the invention also relates to microbicidal compositions and to the use of the compounds of formula I for controlling phytopathogenic microorganisms, in particular phytopathogenic fungi, and for the preventive treatment of plants and stored goods of vegetable or animal origin to protect them from attack by such micro-organisms.

The present invention also relates to the preparation of agrochemical compositions, which comprises homogeneously mixing the active ingredient (compound of formula I) with one or more substances or groups of substances described herein. The invention further relates to a method of treating plants or storable goods, which comprises applying the compounds of formula I or the novel compositions to said plants, parts of plants or to the locus thereof, or to the substrate.

Target crops to be protected within the scope of the present invention comprise e.g. the following species of plants: cereals (wheat, barley, rye, oats, rice, sorghum and related crops), beet (sugar beet and fodder beet), drupes, pomes and soft fruit (applies, pears, plums, peaches, almonds, cherries, strawberries, rasberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

For storage protection, the compounds of formula I are used in unmodified form or, preferably, together with the adjuvants conventionally employed in the art of formulation, and are therefore formulated in known manner to e.g. emulsifiable concentrates, brushable pastes, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, and the formulation of the composition, are chosen in accordance with the intended objectives and the prevailing circumstances. Suitable rates of application are in general in the range from 0.01 to at most 2 kg of active ingredient per 100 kg of substrate to be protected. However, they depend very materially on the nature (surface area, consistency, moisture content) of the substrate and its environmental influences.

Within the scope of this invention, storable goods will be understood as meaning natural substances of vegetable and/or animal origin and the products obtained therefrom by further processing, for example the plants listed below whose natural life cycle has been interrupted and the parts thereof (stalks, leaves, tubers, seeds, fruits, grains) which are in freshly harvested or further processed form (predried, moistened, crushed, ground, roasted). The following produce may be cited by way of example, without any restriction to the field of use within the scope of this invention: cereals (wheat, barley, rye, oats, rice, sorghum and related crops); beet (carrots, sugar beet and fodder beet); drupes, pomes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconuts, castor oil plants, cocoa beans, groundnuts); cucmber plants (cucumber, marrows, melons); fibre plants (cotton, flax, hemp, jute, ramie); citrus fruit; vegetables (spinach, lettuce, asparagus, cabbages, carrots, anions, tomatoes, potatoes, paprika); lauraceae (avocados, cinnamon, camphor), or maize, tobacco, nuts, coffee, sugar cane, tea, vines, chestnuts, hops, bananas, grass and hay.

Examples of natural products of animal origin are, in particular, dried meat and processed fish products such as dry-cured meat, dry-cured fish, meat extracts, bone meal, fish meal and animal dry feeds.

The storable goods treated with compounds of the formula I are given lasting protection from attack by mould fungi and other harmful microorganisms. The formation of toxic and in some cases carcinogenic mould fungi (aflatoxins and ochratoxins) is inhibited, the goods are preserved from deterioration, and their quality is maintained over a prolonged period of time. The method of the invention is susceptible of application to all forms of dry and moist storable goods which are susceptible to attack by microorganisms such as yeast fungi, bacteria and, in particular, mould fungi.

A preferred method of applying active ingredient comprises spraying or wetting the substrate with a liquid formulation, or mixing the substrate with a solid formulation, of the active ingredient. The invention also relates to the described method of preserving storable goods.

The compounds of formula I are normally applied in the form of compositions and can be applied to the crop area, plant or substrate to be treated, simultaneously or in succession, with further compounds. These compounds can be both fertilisers or micronutrient donors or other preparations that influence plant growth. They can also be selective herbicides, fungicides, bactericides, nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of the formula I or an agrochemical composition which contans at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmalogenes or cardiolipin, which can be obtained e.g. from animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphosphatidyl choline.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one C8–C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide. In the field of storage protection, the auxiliaries which are acceptable for human and animal nutrition are preferred.

The surfactants customarily employed in the art of formulation are described e.g. in "McCutcheon's Detergents and Emulsifiers Annual", MC Publishing Corp. Ridgewood, N.J., 1981; Helmut Stache "Tenside-Taschenbuch" (Tenside Handbook) Carl Hanser Verlag, Munich/Vienna, 1981.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further auxiliaries such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES

Example P1

Preparation of

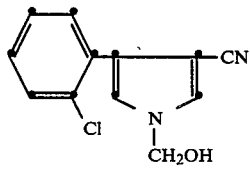

(compound 1.1)

N-Hydroxymethyl-3-(2-chlorophenyl)-4-cyanopyrrole 60.8 g of 3-(2-chlorophenyl)-4-cyanopyrrole, 9.9 g of paraformaldehyde and 0.8 g of triethylamine are thoroughly mixed and and the mixture is then heated, with stirring, at a bath temperature of 90° C. The resultant melt is cooled to room temperature after 1¼ hours, when it congeals to a glass-like solid. Recrystallisation from toluene yields the title compound in the form of brownish crystals of m.p. 94°–97° C.

Example P2

Preparation of

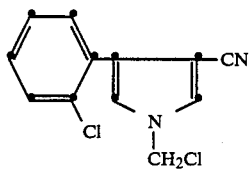

(compound 2.1)

N-Chloromethyl-3-(2-chlorophenyl)-4-cyanopyrrole

With efficient stirring, 48 g of N-hydroxymethyl-3-(2-chlorophenyl)-4-cyanopyrrole are added in several portions to 60 ml of thionyl chloride such that moderate gas evolution is maintained. When the evolution of gas ceases, the mixture is stirred for 2 hours at room temperature and then for 2½ hours at 35°–40° C. After cooling to room temperature, toluene is added and the mixture is concentrated. The residue is recrystallised from diethyl ether/petroleum, affording the title compound in the form of beige crystals with a melting point of 97°–99° C.

Example P3

Preparation of

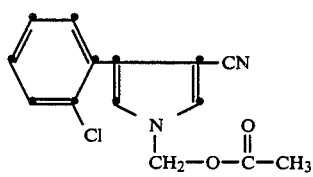

(compound 3.2)

N-Acetyloxymethyl-3-(2-chlorophenyl)-4-cyanopyrrole 41.4 g of N-hydroxymethyl-3-(2-chlorophenyl)-4-cyanopyrrole are dissolved in 350 ml of pyridine and 1.8 g of dimethylaminopyridine are added. Then 21.4 ml of acetic anhydride are slowly added dropwise at 0° to 7° C. and the mixture is stirred for 12 hours. The reaction mixture is then poured into ice-water and extracted twice with ethyl acetate. The extracts are washed twice with dilute ice-cold hydrochloric acid and twice with a semi-saturated aqueous solution of sodium chloride, dried over sodium sulfate and filtered. The filtrate is concentrated and the residue is recrystallised from diethyl ether/hexane to give the title compound in the form of colourless crystals with a melting point of 91°–95° C.

Example P4

Preparation of

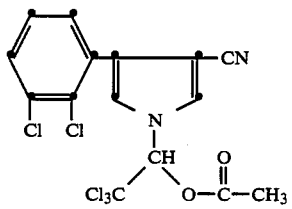

(compound 3.4)

N-(1-Acetyloxy-2,2,2-trichloroethyl)-3-(2,3-dichlorophenyl)-4-cyano pyrrole 1.2 ml of chloral and 1.8 ml of triethylamine are added dropwise in succession to 2.4 g of 3-(2,4-dichlorophenyl)-4-cyanopyrrole in 50 ml of tetrahydrofuran. The reaction mixture is stirred for 1½ hours at 25° C., then 0.1 g of 4-dimethylaminopyridine is added and the mixture is cooled to −10° C. A solution of 0.9 ml of acetyl chloride in 10 ml of tetrahydrofuran is added very slowly dropwise at −10° to −5° C. and the reaction mixture is subsequently stirred for 30 minutes at 0° C. and then for 1 hour at room temperature, and filtered. The filtrate is concentrated and the residue is dissolved in diethyl ether. The ethereal solution is washed twice with a semi-saturated solution of sodium chloride, dried over sodium sulfate, and filtered. The filtrate is concentrated and the crude product is recrystallised from diethyl ether/petroleum ether to give colourless crystals of the title compound with a melting point of 111°–113° C.

Example P5

Preparation of

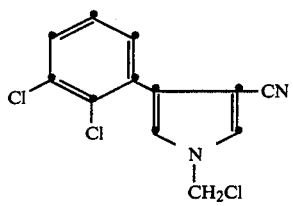

(compound 2.4)

N-Chloromethyl-3-(2,3-dichlorophenyl)-4-cyanopyrrole

To a solution of 23.7 g of 3-(2,3-dichlorophenyl)-4-cyanopyrrole in 300 ml of tetrahydrofuran are added 7.5 g of paraformaldehyde and then 1.5 ml of 1,8-diazabicyclo[5.4.0]undec-7-ene. The mixture is stirred for 3 hours at room temperature. With stirring, 21.7 ml of thionyl chloride are added dropwise at 20°–30° C. to the resultant hydroxymethyl derivative. The reaction mixture is stirred for 16 hours at room temperature, then poured into ice-water and extracted twice with ethyl acetate. The combined organic extracts are washed twice with a halogen-containing solution of sodium chloride, dried over sodium sulfate and filtered. The filtrate is concentrated and the residue is crystallised from ether/petroleum ether to give the title compound in the form of beige crystals with a melting point of 132°–133° C.

Example P6

Preparation of

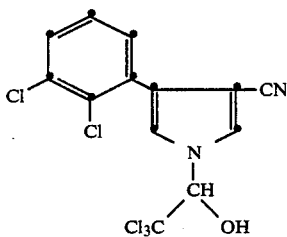

(compound 1.3)

N-(1-Hydroxy)-2,2,2-trichloroethyl)-3-(2,3-dichlorophenyl)-4-cyanopyrrole 39.6 ml of chloral are added dropwise at 20°–29° C. to 64 g of 3-cyano-4-(2,3-dichlorophenyl)pyrrole and 1.2 ml of triethylamine in 400 ml of tetrahydrofuran. Then a further 2.4 ml of triethylamine followed by 1.2 ml of diazabicyclo[5.4.0]undec-7-ene are added and the clear solution so obtained is stirred initially for 2 hours at room temperature and then for 14 hours at 0°–5° C. The solution is then poured into dilute hydrochloric acid and ice and the mixture is extracted twice with ethyl acetate. The organic extracts are washed three times with a cold semi-saturated solution of sodium chloride, dried over sodium sulfate and filtered. The filtrate is concentrated and the residue is crystallised from ether/petroleum ether to give colourless crystals of the desired compound with a melting point of 117° C. (decompos.).

Example P7

Preparation of

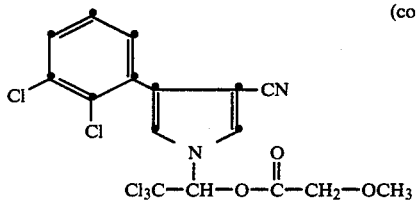

(compound 3.5)

N-[1-(Methoxyacetyloxy)-2,2,2-trichloroethyl]-3-(2,3-dichlorophenyl)-4-cyanopyrrole 4.8 g of 3-cyano-4-(2,3-dichlorophenyl)pyrrole are dissolved in 50 ml of tetrahydrofuran and to the solution are added 0.2 ml of diazabicyclo[5.4.0]undec-7-ene and then 2.3 ml of chloral. The solution is cooled to −5° C., then 3.3 ml of triethylamine are added dropwise. The reaction mixture is stirred for 1 hour at −5° C. and then a solution of 2.2 ml of methoxyacetyl chloride in 10 ml of tetrahydrofuran is slowly added dropwise at −10° to −5° C. After it has been stirred for 1 hour in a thawing cooling bath, the reaction mixture is poured into ice-water and extracted twice with ethyl acetate. The organic extracts are washed twice with cold dilute hydrochloric acid and twice with a cold semi-saturated solution of sodium chloride, then dried over sodium sulfate and filtered. The filtrate is concentrated and the residue is crystallised from petroleum ether, affording colourless crystals of the title compound with a melting point of 88°–90° C.

Example P8

Preparation of

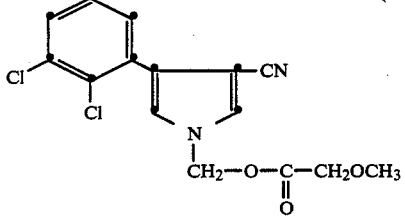

(compound 3.22)

N-[1-(Methoxyacetyloxy)methyl]-3-(2,3-dichlorophenyl)-4-cyanopyrrole 4.5 g of 3-cyano-4-(2,3-dichlorophenyl)pyrrole are dissolved in 50 ml of tetrahydrofuran and to the solution are added 0.65 g of paraformaldehyde, 3.0 ml of triethylamine and 0.5 ml of diazobicyclo[5.4.0]undec-7-ene. The mixture is stirred for 2 hours at room temperature to form a clear solution. With stirring, 2.0 ml of ethoxyacetyl chloride are slowly added dropwise at 5° C. The reaction mixture is kept for 2½ hours at 0°–5° C. and then filtered. The filtrate is concentrated and the residue is crystallised from ether/petroleum ether to give colourless crystals of the title compound with a melting point of 72°–75° C.

The compounds listed in the following tables can also be prepared in corresponding manner.

TABLE 1

Compounds of the formula

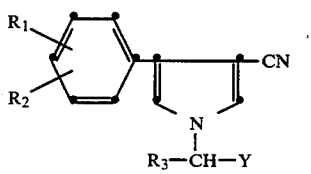

wherein Y is OH.

| Compound | $R_1$ | $R_2$ | $R_3$ | Physical data (°C.) |
|---|---|---|---|---|
| 1.1 | 2-Cl | H | H | m.p. 94–97° |
| 1.2 | H | 3-Cl | H | m.p. 72–74 |
| 1.3 | 2-Cl | 3-Cl | $CCl_3$ | 117° decompos. |
| 1.4 | H | 2-$SCH_3$ | $CCl_3$ | 85° decompos. |
| 1.5 | 2-Cl | H | $CCl_3$ | 70–76° decompos. |
| 1.6 | 2-Cl | 3-Cl | H | m.p. 137–140° |
| 1.7 | H | 3-Cl | $CCl_3$ | |
| 1.8 | 2-$SCH_3$ | H | H | |
| 1.9 | 2-$OCH_3$ | H | H | resin |
| 1.10 | 2-$OCH_3$ | H | $CCl_3$ | |
| 1.11 | H | H | H | m.p. 81–84° |
| 1.12 | H | 3-$OCH_3$ | H | |
| 1.13 | H | 3-$OCH_3$ | $CCl_3$ | resin |
| 1.14 | H | 3-$SCH_3$ | $CCl_3$ | |
| 1.15 | H | 3-$SCH_3$ | H | resin |
| 1.16 | 2-$OCH_3$ | 3-$OCH_3$ | H | |
| 1.17 | 2-$OCH_3$ | 3-$OCH_3$ | $CCl_3$ | |
| 1.18 | H | 3-Br | H | m.p. 65–69° |
| 1.19 | H | 3-Br | $CCl_3$ | |
| 1.20 | H | 3-F | H | m.p. 75–77° |
| 1.21 | 2-F | H | H | |
| 1.22 | H | 3-F | $CCl_3$ | |
| 1.23 | H | 3-I | $CCl_3$ | |
| 1.24 | H | 3-I | H | |

TABLE 2

Compounds of the formula

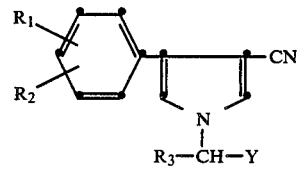

wherein Y is Cl.

| Compound | $R_1$ | $R_2$ | $R_3$ | Physical data (°C.) |
|---|---|---|---|---|
| 2.1 | 2-Cl | H | H | m.p. 97–99° |
| 2.2 | H | 3-Cl | H | m.p. 77–79° |
| 2.3 | 2-Cl | H | $CCl_3$ | |
| 2.4 | 2-Cl | 3-Cl | H | m.p. 132–133° |
| 2.5 | 2-Cl | 3-Cl | $CCl_3$ | m.p. 152–157° |
| 2.6 | H | 3-Cl | $CCl_3$ | |
| 2.7 | 2-$SCH_3$ | H | H | |
| 2.8 | 2-$SCH_3$ | H | $CCl_3$ | |
| 2.9 | 2-$OCH_3$ | H | H | |
| 2.10 | 2-$OCH_3$ | H | $CCl_3$ | |
| 2.11 | H | 3-$OCH_3$ | H | resin |
| 2.12 | H | 3-$OCH_3$ | $CCl_3$ | resin |
| 2.13 | H | 2-$SCH_3$ | H | |
| 2.14 | H | 3-$SCH_3$ | $CCl_3$ | |
| 2.15 | 2-$OCH_3$ | 3-$OCH_3$ | H | |
| 2.16 | 2-$OCH_3$ | 3-$OCH_3$ | $CCl_3$ | |
| 2.17 | H | 3-Br | H | m.p. 71–74° |
| 2.18 | H | 3-Br | $CCl_3$ | semi-crystalline |
| 2.19 | H | 3-F | H | m.p. 80–83° |
| 2.20 | 2-F | H | H | |
| 2.21 | H | 3-F | $CCl_3$ | |
| 2.22 | H | 3-I | $CCl_3$ | |
| 2.23 | H | 3-I | H | m.p. 59–65° |
| 2.24 | H | 3-$OCH_3$ | $CHCl_2$ | |
| 2.25 | H | 3-$OCH_3$ | $CHCl_2$ | resin |
| 2.26 | H | 3-$SCH_3$ | $CH_2Cl$ | |

TABLE 3

Compounds of the formula

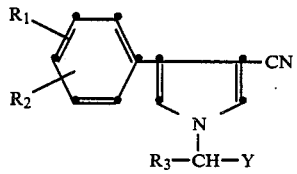

wherein Y is $-OC(O)R_4$.

| Compound | $R_1$ | $R_2$ | $R_3$ | $R_4$ | Physical data (°C.) |
|---|---|---|---|---|---|
| 3.1 | 2-Cl | H | $CCl_3$ | $CH_3$ | m.p. 100–108° |
| 3.2 | 2-Cl | H | H | $CH_3$ | m.p. 91–95° |
| 3.3 | H | 3-Cl | $CCl_3$ | $CH_3$ | m.p. 118–120° |
| 3.4 | 2-Cl | 3-Cl | $CCl_3$ | $CH_3$ | m.p. 111–113° |
| 3.5 | 2-Cl | 3-Cl | $CCl_3$ | $CH_2OCH_3$ | m.p. 88–90° |
| 3.6 | 2-$SCH_3$ | H | $CCl_3$ | $CH_3$ | m.p. 139–141° |
| 3.7 | 2-$OCH_3$ | H | $CCl_3$ | $CH_3$ | m.p. 106–108° |
| 3.8 | 2-Cl | H | H | $CCl_3$ | |
| 3.9 | 2-Cl | H | H | $CH_2OCH_3$ | m.p. 112–114° |
| 3.10 | H | 3-Cl | $CCl_3$ | $CH(CH_3)_2$ | |
| 3.11 | H | 3-Cl | $CCl_3$ | $(CH_2)_3CH_3$ | resin |
| 3.12 | H | 3-Cl | $CCl_3$ | $CH_2Br$ | |
| 3.13 | H | 3-Cl | $CCl_3$ | $CF_3$ | |
| 3.14 | H | 3-Cl | H | $CH_3$ | |
| 3.15 | H | 3-Cl | H | $CHCl_2$ | |
| 3.16 | 2-Cl | 3-Cl | $CCl_3$ | $C_2H_5$ | m.p. 137–141° |
| 3.17 | 2-Cl | 3-Cl | $CCl_3$ | $(CH_2)_3CH_3$ | $n_D^{50}$ 1.5548 |
| 3.18 | 2-Cl | 3-Cl | $CCl_3$ | $CH_2Cl$ | m.p. 143–151° |
| 3.19 | 2-Cl | 3-Cl | $CCl_3$ | H | resin |
| 3.20 | 2-Cl | 3-Cl | H | $CH_3$ | m.p. 95–99° |
| 3.21 | 2-Cl | 3-Cl | H | $C(CH_3)_3$ | m.p. 86–88° |
| 3.22 | 2-Cl | 3-Cl | H | $CH_2OCH_3$ | m.p. 72–75° |

TABLE 3-continued

Compounds of the formula

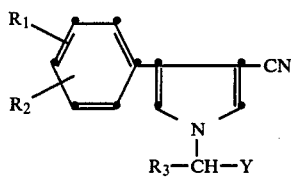

wherein Y is $-OC(O)R_4$.

| Compound | $R_1$ | $R_2$ | $R_3$ | $R_4$ | Physical data (°C.) |
|---|---|---|---|---|---|
| 3.23 | 2-Cl | 3-Cl | H | $CCl_3$ | |
| 3.24 | 2-Cl | 3-Cl | H | H | |
| 3.25 | 2-$OCH_3$ | H | $CCl_3$ | $C(CH_3)_3$ | |
| 3.26 | 2-$OCH_3$ | H | $CCl_3$ | $CH_2Cl$ | resin |
| 3.27 | 2-$OCH_3$ | H | $CCl_3$ | H | |
| 3.28 | 2-$OCH_3$ | H | H | $CCl_3$ | |
| 3.29 | 2-$OCH_3$ | H | H | $CH_3$ | |
| 3.30 | 2-$OCH_3$ | H | H | $CH_2OCH_3$ | semi-crystalline |
| 3.31 | 2-$SCH_3$ | H | $CCl_3$ | $C_2H_5$ | |
| 3.32 | 2-$SCH_3$ | H | $CCl_3$ | $CH_2Cl$ | |
| 3.33 | 2-$SCH_3$ | H | $CCl_3$ | $CH_2OCH_3$ | semi-crystalline |
| 3.34 | 2-$SCH_3$ | H | H | $CH_3$ | |
| 3.35 | 2-$SCH_3$ | H | H | $C_2H_5$ | |
| 3.36 | 2-$SCH_3$ | H | H | $CCl_3$ | |
| 3.37 | 2-Cl | 3-Cl | H | $CH_2Cl$ | m.p. 113–115° |
| 3.38 | 2-Cl | 3-Cl | H | $C_2H_5$ | resin |
| 3.39 | 2-Cl | 3-Cl | H | $C_4H_9-n$ | $n_D^{50}$ 1.5571 |
| 3.40 | 2-Cl | 3-Cl | $CCl_3$ | $C(CH_3)_3$ | m.p. 146–147° |
| 3.41 | H | H | $CCl_3$ | $CH_2OCH_3$ | m.p. 121–122° |
| 3.42 | 2-Cl | 3-Cl | $CCl_3$ | $C_2H_5$ | semi-crystalline |
| 3.43 | 2-Cl | 3-Cl | H | $CH_2Br$ | m.p. 88–90° |
| 3.44 | 2-Cl | 3-Cl | $CCl_3$ | $CH_2Br$ | m.p. 132–135° |
| 3.45 | 2-Cl | 3-Cl | $CCl_3$ | $CH_2OC_2H_5$ | m.p. 115–117° |
| 3.46 | 2-Cl | 3-Cl | H | $CH_2OC_2H_5$ | m.p. 83–85° |
| 3.47 | 2-Cl | H | $CCl_3$ | $CH_2OCH_3$ | m.p. 116–118° |
| 3.48 | H | H | H | $CH_2OCH_3$ | m.p. 78–79° |
| 3.49 | 2-Cl | 3-Cl | H | $CH_2OC_3H_7-n$ | m.p. 87–88° |
| 3.50 | 2-Cl | 3-Cl | $CCl_3$ | $CH_2OC_3H_7-n$ | m.p. 76–78° |
| 3.51 | 2-Cl | 3-Cl | H | $CH_2OC_4H_9-n$ | m.p. 71–74° |
| 3.52 | 2-Cl | 3-Cl | $CCl_3$ | $CH_2OC_4H_9-n$ | m.p. 89–91° |
| 3.53 | 2-Cl | 3-Cl | H | $CH_2OC_6H_{13}-n$ | |
| 3.54 | 2-Cl | 3-Cl | $CCl_3$ | $CH_2OC_6H_{13}-n$ | |
| 3.55 | 2-Cl | H | H | $CH_2OCH(CH_3)_2$ | |
| 3.56 | 2-Cl | H | $CCl_3$ | $CH_2OCH(CH_3)_2$ | m.p. 69–76° |
| 3.57 | 2-Cl | 3-Cl | H | $CH_2OCH(CH_3)_2$ | m.p. 74–75° |
| 3.58 | 2-Cl | 3-Cl | $CCl_3$ | $CH_2OCH(CH_3)_2$ | m.p. 112–115° |
| 3.59 | 2-Cl | 3-Cl | H | $CH_2OCH(CH_3)C_2H_5$ | m.p. 71–73° |
| 3.60 | 2-Cl | 3-Cl | $CCl_3$ | $CH_2OCH(CH_3)C_2H_5$ | m.p. 70–74° |
| 3.61 | 2-Cl | 3-Cl | H | $CH_2OC(CH_3)_3$ | |
| 3.62 | 2-Cl | 3-Cl | $CCl_3$ | $CH_2OC(CH_3)_3$ | |
| 3.63 | 2-Cl | H | H | $CH_2OCH_2CH_2OCH_3$ | |
| 3.64 | 2-Cl | H | $CCl_3$ | $CH_2OCH_2CH_2OCH_3$ | |
| 3.65 | 2-Cl | 3-Cl | H | $CH_2OCH_2CH_2OCH_3$ | m.p. 99–101° |
| 3.66 | 2-Cl | 3-Cl | $CCl_3$ | $CH_2OCH_2CH_2OCH_3$ | $n_D^{50}$ 1.5472 |
| 3.67 | 2-Cl | 3-Cl | H | $CH_2OCH_2CH=CH_2$ | m.p. 65–67° |
| 3.68 | 2-Cl | 3-Cl | $CCl_3$ | $CH_2OCH_2CH=CH_2$ | m.p. 86–88° |
| 3.69 | 2-Cl | 3-Cl | H | $CH_2OCH_2C\equiv CH$ | m.p. 109–111° |
| 3.70 | 2-Cl | 3-Cl | $CCl_3$ | $CH_2OCH_2C\equiv CH$ | $n_D^{50}$ 1.5732 |
| 3.71 | 2-Cl | 3-Cl | H | $CH_2OC_6H_5$ | m.p. 119–121° |
| 3.72 | 2-Cl | 3-Cl | $CCl_3$ | $CH_2OC_6H_5$ | $n_D^{50}$ 1.5803 |
| 3.73 | 2-Cl | 3-Cl | H | $CH_2OC_6H_3Cl_2(3,5)$ | m.p. 125–127° |
| 3.74 | 2-Cl | 3-Cl | $CCl_3$ | $CH_2OC_6H_3Cl_2(3,5)$ | m.p. 154–156° |
| 3.75 | 2-Cl | 3-Cl | H | $CH_2OC_6H_3Cl_2(2,4)$ | m.p. 102–104° |
| 3.76 | 2-Cl | 3-Cl | $CCl_3$ | $CH_2OC_6H_3Cl_2(2,4)$ | m.p. 157–159° |
| 3.77 | 2-Cl | H | H | 2-tetrahydrofuryl | $n_D^{50}$ 1.5672 |
| 3.78 | 2-Cl | H | $CCl_3$ | 2-tetrahydrofuryl | m.p. 142–149° |
| 3.79 | 2-Cl | 3-Cl | H | 2-tetrahydrofuryl | m.p. 96–98° |
| 3.80 | 2-Cl | 3-Cl | $CCl_3$ | 2-tetrahydrofuryl | m.p. 156–160° |
| 3.81 | 2-Cl | H | H | $CH_2SCH_3$ | |
| 3.82 | 2-Cl | H | $CCl_3$ | $CH_2SCH_3$ | |
| 3.83 | H | H | H | $CH_2SCH_3$ | |
| 3.84 | H | H | $CCl_3$ | $CH_2SCH_3$ | |
| 3.85 | 2-Cl | 3-Cl | H | $CH_2SCH_3$ | |
| 3.86 | 2-Cl | 3-Cl | $CCl_3$ | $CH_2SCH_3$ | |
| 3.87 | 2-Cl | 3-Cl | H | $CH_2SCH(CH_3)C_2H_5$ | resin |
| 3.88 | 2-Cl | 3-Cl | $CCl_3$ | $CH_2SCH(CH_3)C_2H_5$ | |
| 3.89 | 2-Cl | H | H | $CH_2SCH(CH_3)C_2H_5$ | |

TABLE 3-continued

Compounds of the formula

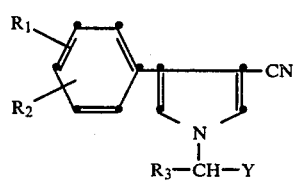

wherein Y is —OC(O)R$_4$.

| Compound | R$_1$ | R$_2$ | R$_3$ | R$_4$ | Physical data (°C.) |
|---|---|---|---|---|---|
| 3.90 | 2-Cl | H | CCl$_3$ | CH$_2$SCH(CH$_3$)C$_2$H$_5$ | |
| 3.91 | 2-Cl | 3-Cl | H | CH$_2$SC$_4$H$_9$—n | |
| 3.92 | 2-Cl | 3-Cl | CCl$_3$ | CH$_2$SC$_4$H$_9$—n | |
| 3.93 | 2-Cl | 3-Cl | H | CH$_2$SC(CH$_3$)$_3$ | |
| 3.94 | 2-Cl | 3-Cl | CCl$_3$ | CH$_2$SC(CH$_3$)$_3$ | |
| 3.95 | 2-Cl | 3-Cl | H | C(O)OC$_2$H$_5$ | m.p. 111–113° |
| 3.96 | 2-Cl | H | H | CH$_2$SC$_6$H$_5$ | |
| 3.97 | 2-Cl | H | CCl$_3$ | CH$_2$SC$_6$H$_5$ | |
| 3.98 | 2-Cl | 3-Cl | H | CH$_2$SC$_6$H$_5$ | |
| 3.99 | 2-Cl | 3-Cl | CCl$_3$ | CH$_2$SC$_6$H$_5$ | |
| 3.100 | 2-Cl | H | H | CH=CH$_2$ | |
| 3.101 | 2-Cl | H | CCl$_3$ | CH=CH$_2$ | |
| 3.102 | 2-Cl | 3-Cl | H | CH=CH$_2$ | |
| 3.103 | 2-Cl | 3-Cl | CCl$_3$ | CH=CH$_2$ | m.p. 106–108° |
| 3.104 | 2-Cl | 3-Cl | H | CH=CH—CH$_3$ | |
| 3.105 | 2-Cl | 3-Cl | CCl$_3$ | CH=CH—CH$_3$ | m.p. 107–109° |
| 3.106 | 2-Cl | H | H | CH=CH—CH$_3$ | |
| 3.107 | 2-Cl | H | CCl$_3$ | CH=CH—CH$_3$ | |
| 3.108 | H | H | H | CH$_2$Cl | m.p. 83–84° |
| 3.109 | H | 3-OCH$_3$ | H | CH$_3$ | |
| 3.110 | H | 3-OCH$_3$ | CCl$_3$ | CH$_3$ | |
| 3.111 | H | 3-OCH$_3$ | CCl$_3$ | CH$_3$ | |
| 3.112 | H | 3-OCH$_3$ | H | CH$_3$ | resin |
| 3.113 | 2-OCH$_3$ | 3-OCH$_3$ | H | CH$_2$OCH$_3$ | resin |
| 3.114 | 2-OCH$_3$ | 3-OCH$_3$ | H | CH$_3$ | |
| 3.115 | H | 3-Br | CCl$_3$ | CH$_2$OCH$_3$ | |
| 3.116 | H | 3-Br | H | CH$_3$ | |
| 3.117 | H | 3-F | H | CH$_3$ | |
| 3.118 | 2-F | H | H | CH$_2$OCH$_3$ | |
| 3.119 | H | 3-F | CCl$_3$ | CH$_3$ | |

FORMULATION EXAMPLES

Formulation Examples for liquid active ingredients of the formula I (throughout, percentages are by weight)

| F1. Emulsifiable concentrates | (a) | (b) | (c) |
|---|---|---|---|
| a compound of tables 1 to 3 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| F2. Solutions | (a) | (b) | (c) | (d) |
|---|---|---|---|---|
| a compound of tables 1 to 3 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| F3. Granulates | (a) | (b) |
|---|---|---|
| a compound of tables 1 to 3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4. Dusts | (a) | (b) |
|---|---|---|
| a compound of tables 1 to 3 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| F5. Wettable powders | (a) | (b) | (c) |
|---|---|---|---|
| a compound of tables 1 to 3 | 25% | 50% | 75% |
| sodium lignosulfonate | 5% | 5% | — |
| sodium lauryl sulfate | 3% | — | 5% |

| F5. Wettable powders | (a) | (b) | (c) |
|---|---|---|---|
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thorougly ground in a suitable mill, affording wettable powders which can be diluted with water to give suspensions of the desired concentration.

| F6. Emulsifiable concentrate | |
|---|---|
| a compound of tables 1 to 3 | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F7. Dusts | (a) | (b) |
|---|---|---|
| a compound of tables 1 to 3 | 5% | 8% |
| talcum | 95% | — |
| kaolin | — | 92% |

Ready-for use dusts are obtained by mixing the active ingredient with the carriers, and grinding the mixture in a suitable mill.

| F8. Extruder granulate | |
|---|---|
| a compound of tables 1 to 3 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a strem of air.

| F9. Coated granulate | |
|---|---|
| a compound of tables 1 to 3 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| F10. Suspension concentrate | |
|---|---|
| a compound of tables 1 to 3 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% | 0.8% |

| F10. Suspension concentrate | |
|---|---|
| aqueous emulsion water | 32% |

The finely ground active ingredient is intimately mixed with the aduvants, giving a suspension concentrate from which suspensions of any desired concentration can be obtained by dilution with water.

BIOLOGICAL EXAMPLES

EXAMPLE B1

Action against Puccinia graminis on wheat
(a) Residual-protective action

Wheat plants were treated 6 days after sowing with a spray mixture prepared from a wettable powder formulation of the test compound (0.06%). After 24 hours the treated plants were infected with a uredospore suspension of the fungus. The infected plants were incubated for 48 hours at 95–100% relative humidity and about 20° C. and then stood in a greenhouse at about 22° C. Evaluation of rust pustule development was made 12 days after infection.

(b) Systemic action

Wheat plants were treated 5 days after sowing with a spray mixture prepared from a wettable powder formulation of the test compound (0.006% based on the volume of the soil). After 48 hours the treated plants were infected with a uredospore suspension of the fungus. The plants were then incubated for 48 hours at 95–100% relative humidity and about 20° C. and then stood in a greenhouse at about 22° C. Evaluation or rust pustule development was made 12 days after infection.

Compounds of Tables 1 to 3 were very effective against Puccinia fungi not only in the above greenhouse test but also in field trials. Puccinia attack was 100% on untreated and infected control plants. Compounds No. 1.2 to 1.5, 1.9, 1.13, 2.11, 2.12, 2.18, 3.2, 3.4 to 3.7, 3.37 to 3.40, 3.42 to 3.46, 3.51, 3.52, 3.57, 3.70, 3.73 to 3.76 and 3.94 and others inhibited Puccinia attack to 0 to 10%.

EXAMPLE B2

Action against Cercospora arachidicola in groundnut plants

Residual protective action

Groundnut plants 10–15 cm in height were sprayed with a spray mixture (0.006%) prepared from a wettable powder formulation of the test compound, and infected 48 hours later with a conidia suspension of the fungus. The infected plants were incubated for 72 hours at about 21° C. and high humidity and then stood in a greenhouse until the typical leaf specks occur. Evaluation of the fungicidal action was made 12 days after infection and was based on the number and size of the specks.

(b) Systemic action

Groundnut plants 10–15 cm in height were sprayed with a spray mixture prepared from a wettable powder formulation of the test compound (0.06%, based on the volume of the soil). The treated plants were infected 48 hours later with a conidia suspension of the fungus and then incubated for 72 hours at about 21° C. and high humidity. The plants were then stood in a greenhouse and evaluation of fungus attack was made 11 days later.

Compared with untreated and infected control plants (number and size of the specks=100%), Cercospora attack on groundnut plants treated in the greenhouse or in the field with compounds of Tables 1 to 3 was substantially reduced. Thus compounds 1.3, 1.6, 3.4, 3.5, 3.17, 3.18, 3.20, 3.49, 3.51, 3.52, 3.57, 3.67, 3.69, 3.70 and 3.95 inhibited Cercospora attack almost completely (8%).

EXAMPLE B3

Action against Botrytis cinerea on beans
Residual protective action

Bean plants about 10 cm in height were sprayed with a spray mixture (0.02%) prepared from a wettable powder formulation of the test compound. After 48 hours the treated plants were infected with a conidia suspension of the fungus. The infected plants were incubated for 3 days at 95–100% relative humidity and 21° C. and then evaluated for fungus attack. The compounds of Tables 1 to 3 inhibited the fungus infection very strongly not only in the above model test but also in field trials. At a concentration of 0.02%, compounds 1.1 to 1.6, 1.9, 1.11, 1.13, 1.15, 1.18, 1.20, 2.1, 2.2, 2.4, 2.5, 2.11, 2.12, 2.17, 2.18, 2.19, 2.23, 3.1 to 3.7, 3.9, 3.16 to 3.22, 3.26, 3.30, 3.33, 3.37, 3.38, 3.39 to 3.52, 3.56 to 3.60, 3.65 to 3.80, 3.95, 3.103, 3.105, 3.108, 3.112 and 3.113 were fully effective (0 to 5% attack). This activity was achieved with some representatives at half the rate of application. Fungus attack was 100% on untreated and infected bean plants. The intermediates 16 and 24 were equally effective.

EXAMPLE B4

Action against Botrytis cinerea on apples

Artificially damaged apples were treated by dropping a spray mixture prepared from the respective test compound formulated as wettable powder onto the injury sites. The treated fruit was then inoculated with a spore suspension of Botrytis cinerea and incubated for 1 week at high humidity and about 20° C. Evaluation was made by counting the number of injury sites attacked by rot and deducing the fungicidal action of the test compound therefrom. Compared with untreated controls (100% attack), compounds 1.1 to 1.6, 1.9, 1.11, 1.13, 1.15, 1.18, 1.20, 2.1, 2.2, 2.4, 2.5, 2.11, 2.12, 2.17, 2.18, 2.19, 2.23, 3.1 to 3.7, 3.9, 3.16 to 3.22, 3.26, 3.30, 3.33, 3.37, 3.38, 3.39 to 3.52, 3.56 to 3.60, 3.65 to 3.80, 3.95, 3.103, 3.105, 3.108, 3.112 and 3.113 and others inhibited fungus attack almost completely. The intermediates 16 and 24 were also equally effective.

EXAMPLE B5

Action against Piricularia on rice plants
Residual protective action

After a cultivation period of 2 weeks, rice plants were sprayed with a spray mixture (0.02%) prepared from a wettable powder formulation of the test compound. After 48 hours the treated plants were infected with a conidia suspension of the fungus. Evaluation of fungus attack was made after incubation for 5 days at 95–100% relative humidity and 24° C. Compounds of formula I inhibited Piricularia attack effectively e.g. compounds 1.3, 1.6, 2.2, 2.4, 3.1 to 3.5, 3.7, 3.17, 3.18, 3.20, 3.21, 3.44 to 3.47, 3.49, 3.51, 3.52, 3.57, 3.67, 3.70, 3.75 and 3.95. These compounds reduced attack to less than 10%. It was also possible to achieve this activity under field conditions.

EXAMPLE B6

Action against Rhizoctonia solani in cabbage
Action after soil application

The fungus was cultivated on sterile millet seeds and added to a mixture of soil and sand. Dishes were filled with the infected soil in which cabbage seeds were sown. Immediately after sowing, an aqueous suspension of the test compound formulated as wettable powder was poured onto the soil (20 ppm, based on the volume of the soil). The dishes were then put into a greenhouse for 2–3 weeks at about 24° C. and kept uniformly moist by light spraying. The test was evaluated by determining the number of emerged cabbage plants. After treatment with wettable powders which contained one of compounds 1.3, 2.1, 3.20 or 3.27, 80% of the cabbage seeds emerged and the plants had a healthy appearance.

EXAMPLE B7

Residual-protective action against Venturia inaequalis on apple shoots

Apple cuttings with 10–20 cm long fresh shoots were sprayed with a spray mixture (0.006%) prepared from a wettable powder formulation of the test compound. The plants were infected 24 hours later with a conidia suspension of the fungus. The plants were then incubated for 5 days at 90–100% relative humidity and stood in a greenhouse for a further 10 days at 20°–24° C. Evaluation of scab infestation was made 15 days after infection.

Compounds of formula I were very effective against Venturia pathogens. Compared with attack on untreated control plants, scab attack was inhibited to less than 20% with compounds 1.2, 1.3, 3.4, 3.5, 3.17, 3.18, 3.20, 3.22, 3.37, 3.39, 3.71 and 3.95. This effect was achieved in field trials with compounds 1.2, 1.3, 3.4, 3.5 and 3.17 in field trials even at a concentration of 0.002%.

EXAMPLE B8

Action against Helminthosporium gramineum

Wheat grains were contaminated with a spore suspension of the fungus and dried. The contaminated grains were dressed with a suspension of the test compound prepared from a wettable powder (600 ppm of test compound, based on the weight of the seeds). Two days later the grains were placed in suitable agar dishes and a count of the fungus colonies which had developed around the grains was made after another 4 days. The effectiveness of the test compounds was assessed on the basis of the number and size of the colonies. Compounds of Tables 1 to 3, in particular those of Table 3, inhibited fungus attack substantially (0 to 10%).

EXAMPLE B9

Action against Fusarium nivale

Wheat grains were contaminated with a spore suspension of the fungus and dried. The contaminated grains were dressed with a suspension of the test compound prepared from a wettable powder (600 ppm of test compound, based on the weight of the seeds). Two days later the grains were placed in suitable agar dishes and a count of the fungus colonies which had developed around the grains was made after another 4 days. The effectiveness of the test compounds was assessed on the basis of the number and size of the colonies. The development of fungus colonies was almost completely inhibited (0 to 5%) on wheat grains treated with a wettable powder formulation of one of the compounds of Tables 1 to 3.

EXAMPLE B10

Grain preservative test (a) Short-term test against mould fungi on moist maize

Dry maize kernels (80 g portions) intended for use as animal feed were thoroughly mixed in sealable platic beakers with compounds of all Tables in the form of an aqueous suspension, emulsion or solution. The application of test compound was made so as to give a concentration of 0.06%, based on the dry weight of the maize. A moistened sheet of paper ensured a saturated moist atmosphere in the beakers, which were filled with the maize and then sealed. After an incubation of 2-3 weeks at about 20° C., a mixed population of mould fungi developed spontaneously on the maize samples treated only with water. There was no need to make an artificial infection. The effectiveness of the compounds of the formula I was evaluated by determining the extent of fungus development after 3 weeks.

(b) Long-term test against mould fungi on moist maize

I The maize samples exhibiting no fungus attack after 3 weeks were incubated for a further two months. A visual assessment was made after each month, applying the same criteria as in test (a).

II The test procedure was in principle the same as in (a) and (b), except that the test compound of the formula I or II' were used in concentrations of 2000, 600 and 200 ppm a.i. (based on the dry weight of the maize) over 6 months.

In all three tests (a), (bI) and (bII), the formation of mould fungi on moist maize was inhibited completely both short-term (3 weeks) and long-term (6 months) by treatment with compounds of the formula I of Tables 1 to 3. For example, compounds 1.1 to 1.6, 1.9, 1.11, 1.13, 1.15, 1.18 and a number of representatives of Tables 2 and 3 in all three tests (a), (bI) and (bII) inhibited mould fungus attack almost completely (0-5% attack) at a test concentration of 600 ppm a.i.. Treatment with compounds of the formula I in similar tests using, alternatively, cereals (oats), hay, carrot chips or broad beans instead of fodder maize, gave similar reuslts of long-term protection over several months.

What is claimed is:

1. A compound of the formula I

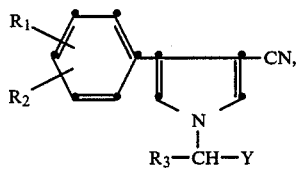

(I)

wherein $R_1$ and $R_2$, each independently of the other, are hydrogen, halogen, methoxy or methylthio, $R_3$ is hydrogen or $C_1$–$C_8$haloalkyl, Y is hydroxy, halogen or the —O—C(O)—$R_4$ group, and $R_4$ is hydrogen, $C_1$–$C_8$alkyl, $C_1$–$C_8$haloalkyl, $C_2$–$C_6$alkenyl, 2-tetrahydrofuryl, 2-tetrahydropyranyl, $C_1$–$C_6$alkoxycarbonyl or the —CH($R_5$)—$XR_6$ group, wherein X is oxygen or sulfur, $R_5$ is hydrogen or $C_1$–$C_3$alkyl, and $R_6$ is $C_1$–$C_6$alkyl, ($C_1$–$C_6$alkoxy)-$C_1$–$C_6$alkyl, $C_3$–$C_6$alkenyl, $C_3$–$C_6$alkynyl, phenyl or phenyl which is substituted by halogen, $C_1$–$C_6$alkyl, $C_1$–$C_6$alkoxy, and/or $C_1$–$C_6$alkoxycarbonyl.

2. A compound of the formula I according to claim 1, wherein $R_1$ is in the 2-position and $R_2$ is in the 3-position of the phenyl ring and each independently of the other is hydrogen, halogen, methoxy or methylthio; $R_3$ is hydrogen or $C_1$–$C_4$haloalkyl; and Y is hydroxy, halogen or the —O—C(O)—$R_4$ group, wherein $R_4$ is $C_1$–$C_6$alkyl, $C_1$–$C_6$haloalkyl, 2-tetrahydrofuryl, 2-tetrahydropyranyl, $C_1$–$C_2$alkoxycarbonyl or the —CH($R_5$)—$XR_6$ group, wherein X is oxygen or sulfur, $R_5$ is hydrogen or methyl and $R_6$ is $C_1$–$C_6$alkyl, ($C_1$–$C_3$alkoxy)-$C_1$–$C_3$alkyl, $C_3$–$C_6$alkenyl, $C_3$–$C_6$alkynyl, phenyl or phenyl which is substituted by fluorine, chlorine, bromine, methyl, methoxy and/or $C_1$–$C_3$alkoxycarbonyl.

3. A compound of the formula I according to claim 2, wherein $R_1$ is hydrogen, 2-Cl, 2-methoxy or 2-methylthio; $R_2$ is hydrogen or 3—Cl; $R_3$ is hydrogen or $C_1$–$C_4$ haloalkyl; and Y is OH, chlorine or the —O—C(O)—$R_4$ group, wherein $R_4$ is $C_1$–$C_4$alkyl, $C_1$–$C_3$haloalkyl, 2-tetrahydrofuryl, 2-tetrahydropyranyl, $C_1$–$C_2$alkoxycarbonyl or the —CH$_2$—O$_6$ group, wherein $R_6$ is $C_1$–$C_4$alkyl, ($C_1$–$C_3$alkoxy)-$C_1$$C_3$alkyl, $C_3$–$C_6$alkenyl or $C_3$–$C_6$-alkynyl, phenyl or phenyl which is substituted by fluorine, chlorine, bromine, methyl, methoxy, ethoxycarbonyl and/or methoxycarbonyl.

4. A compound of the formula I according to claim 2, wherein $R_1$ is hydrogen, 2-Cl, 2-methoxy or 2-methylthio; $R_2$ is hydrogen or 3-Cl; $R_3$ is hydrogen or $CCl_3$; and Y is OH, chlorine or the —O—C(O)—$R_4$ group, wherein $R_4$ is $C_1$–$C_4$alkyl, $C_1$–$C_2$haloalkyl, 2-tetrahydrofuryl, 2-tetrahydropyranyl, methoxycarbonyl or the —CH$_2$O$R_6$ group, wherein $R_6$ is $C_1$–$C_4$alkyl, methoxymethyl, ethoxymethyl, methoxyethyl, allyl, propargyl, phenyl or phenyl which is substituted by fluorine, chlorine, bromine, methyl, methoxy and/or methoxycarbonyl.

5. A compound of the formula I according to claim 1, selected from the group consisting of:

N-(hydroxymethyl)-3-(3-chlorophenyl)-4-cyanopyrrole,

N-(1-hydroxy-2,2,2-trichloroethyl)-3-(2-methylthiophenyl)-4-cyanopyrrole,

N-(chloromethyl)-3-(3-methoxyphenyl)-4-cyanopyrrole,

N-(1,2,2,2-tetrachloroethyl)-3-(3-methoxyphenyl)-4-cyanopyrrole,

N-(1,2,2,2-tetrachloroethyl)-3-(3-bromophenyl)-4-cyanopyrrole.

6. A compound of the formula I according to claim 2, selected from the group consisting of:

N-(1-acetyloxy-2,2,2-trichloroethyl)-3-(2,3-dichlorophenyl)-4-cyanopyrrole,

N-(1-hydroxy-2,2,2-trichloroethyl)-3-(2,3-dichlorophenyl)-4-cyanopyrrole,

N-(1-methoxyacetyloxy-2,2,2-trichloroethyl)-3-(2,3-dichlorophenyl)-4-cyanopyrrole, N-(methoxyacetyloxymethyl)-3-(2,3-dichlorophenyl)-4-cyanopyrrole, N-[1-(n-butylcarbonyloxy)-2,2,2-trichloroethyl]-3-(2,3-dichlorophenyl)-4-cyanopyrrole, N-[1-(n-propoxyacetyloxy)-2,2,2-trichloroethyl]-3-(2,3-dichlorophenyl)-4-cyanopyrrole, N-[1-(n-butoxyacetyloxy)-2,2,2-trichloroethyl]-3-(2,3-dichlorophenyl)-4-cyanopyrrole, N-[1-(n-butoxyacetyloxy)ethyl]-3-(2,3-dichlorophenyl)-4-cyanopyrrole, N-[1-(propargyloxyacetyloxy)-2,2,2-trichloroethyl]-3-(2,3-dichlorophenyl)-4-cyanopyrrole.

7. A compound of the formula I according to claim 1, selcted from the group consisting of:

N-(1-hydroxy-2,2,2-trichloroethyl)-3-(2-methylthiophenyl)-4-cyanopyrrole,

N-(1-hydroxy-2,2,2-trichloroethyl)-3-(2-methoxyphenyl)-4-cyanopyrrole,

N-(1-hydroxy-2,2,2-trichloroethyl)-3-(2-chlorophenyl)-4-cyanopyrrole,

N-[1-(isopropoxyacetyloxy)-2,2,2-trichloroethyl]-3-(2-chlorophenyl)-4-cyanopyrrole, N-[1-(methoxyacetyloxy)-2,2,2-trichloroethyl]-3-(2-methylthiophenyl)-4-cyanopyrrole, N-(methoxyacetyl)-3-(2-chlorophenyl)-4-cyanopyrrole.

8. A microbicidal composition for controlling phytopathogenic microorganisms or for protecting living plants from attack by such microorganisms and/or for preserving perishable storable goods of vegetable or animal origin comprising an effective amount of at least one compound of the formula I of claim 1.

9. A method of controlling phytopathogenic microorganisms or of protecting cultivated plants from attack by said microorganisms comprising applying to said plants, to parts of plants or to the locus thereof a microbicidally effective amount of a compound of the formula I of claim 1.

10. A method of preserving or protecting storable goods by applying a microbicidally effective amount of a compound of the formula I of claim 1 to said storable goods.

* * * * *